United States Patent [19]

Okazaki et al.

[11] Patent Number: 4,521,605
[45] Date of Patent: Jun. 4, 1985

[54] CARBAZOLE COMPOUNDS AND PROCESS FOR PREPARING THE SAME

[75] Inventors: Hideo Okazaki, Tokyo; Hiroshi Imagome, Urawa; Susumu Suzuka, Yono; Kiyoshi Sakai, Numazu, all of Japan

[73] Assignees: Hodogaya Chemical Co., Ltd.; Ricoh Company, Ltd., both of Tokyo, Japan

[21] Appl. No.: 423,420

[22] Filed: Sep. 24, 1982

[30] Foreign Application Priority Data

Oct. 3, 1981 [JP] Japan .................. 56-157879

[51] Int. Cl.$^3$ .......................... C07D 209/86
[52] U.S. Cl. ........................ 548/440; 430/58; 430/59; 430/79; 548/445
[58] Field of Search .............. 548/440, 445; 542/400, 542/454

[56] References Cited

U.S. PATENT DOCUMENTS

| | | | |
|---|---|---|---|
| 3,796,707 | 3/1974 | Siegrist et al. | 542/454 |
| 3,955,984 | 5/1976 | Kobayashi et al. | 542/400 X |
| 4,001,130 | 1/1977 | Schinzel et al. | 542/400 X |
| 4,184,871 | 1/1980 | Oba et al. | 542/454 UX |
| 4,293,492 | 10/1981 | Sasaki et al. | 548/440 X |

OTHER PUBLICATIONS

Drefahl, et al., Ber., 95, (1962), pp. 2775–2781.
"The Merck Index", 8th Ed., (1968), pp. 1226–1227.

*Primary Examiner*—Joseph Paul Brust
*Attorney, Agent, or Firm*—Flynn, Thiel, Boutell & Tanis

[57] ABSTRACT

Carbazole compounds of formula (I) are disclosed, which are useful as photoconductors for electrophotography and fluorescent brightening agent in the field of paints,

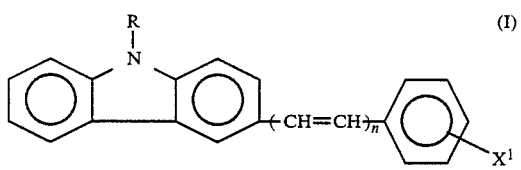
(I)

wherein R represents a $C_{2\sim4}$ alkyl group, or a benzyl group; $X^1$ represents hydrogen, a $C_{1\sim4}$ alkyl group, a $C_{1\sim4}$ alkoxyl group, a halogen atom, a nitro group, an amino group, a $C_{1\sim4}$ alkylamino group or a benzylamino group; and n is an integer 1 or 2. A method of preparing a carbazole compound of formula (II) is also disclosed, in which a phenyl derivative of formula (III) is caused to react with an aldehyde of formula (IV),

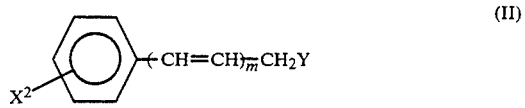
(II)

wherein R represents a $C_{2\sim4}$ alkyl group, or a benzyl group; $X^2$ represents hydrogen, a $C_{1\sim4}$ alkyl group, a $C_{1\sim4}$ alkoxyl group, a halogen atom, a nitro group; and m is an integer 0 or 1;

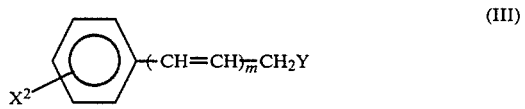

(III)

wherein $X^2$ represents the same as in the formula (II) and Y represents a triphenylphosphonium group of the formula

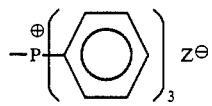

wherein $Z^\ominus$ represents a halogen ion, or Y represents a dialkylphosphonate group of the formula

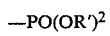

—PO(OR')$_2$ wherein R' represents a $C_{1\sim4}$ alkyl group;

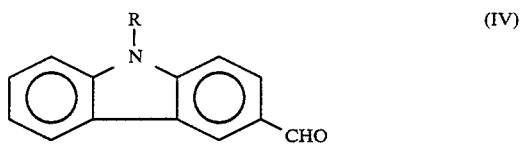

(IV)

wherein R represents the same as in the formula (III).

10 Claims, No Drawings

CARBAZOLE COMPOUNDS AND PROCESS FOR PREPARING THE SAME

BACKGROUND OF THE INVENTION

The present invention relates to novel carbazole compounds and to a process for preparing the same, and more particularly to carbazole compounds of formula (I).

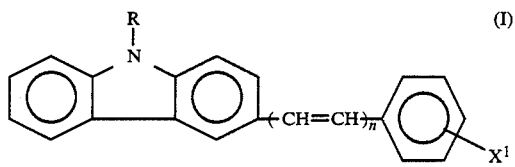

wherein R represents a $C_{2\sim4}$ alkyl group, or a benzyl group; $X^1$ represents hydrogen, a $C_{1\sim4}$ alkyl group, a $C_{1\sim4}$ alkoxy group, a halogen atom, a nitro group, an amino group, a $C_{1\sim4}$ alkylamino group or a benzylamino group; and n is an integer 1 or 2.

The present invention also relates to a process for preparing carbazole compounds of the formula (II) by allowing phenyl derivatives of formula (III) to react with aldehydes of formula (IV):

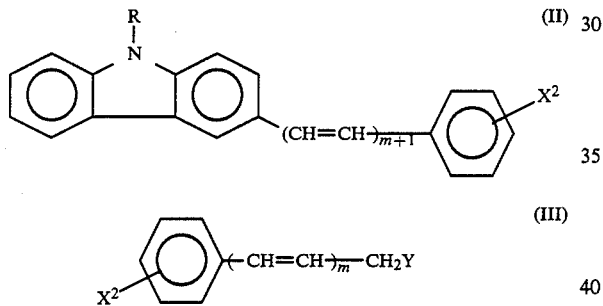

wherein $X^2$ represents hydrogen, a $C_{1\sim4}$ alkyl group, a $C_{1\sim4}$ alkoxy group, a halogen atom or a nitro group; m is an integer 0 or 1; and Y represents a triphenylphosphonium group of the formula

wherein $Z^\ominus$ represents a halogen ion, or Y represents a dialkylphosphonate group of the formula

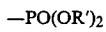

—PO(OR')$_2$ wherein R' represents a $C_{1\sim4}$ alkyl group.

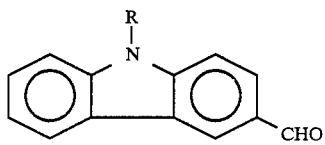

wherein R represents a $C_{2\sim4}$ alkyl group, or a benzyl group.

The thus prepared carbazole compounds according to the present invention are useful as organic photoconductor materials for use in electrophotography, and as fluorescent brightening agents.

Generally, in the art of electrophotography, a photoconductor is electrically charged, for example, by corona charging in the dark, and is then exposed to a light image which selectively dissipates the charges in the illuminated areas of the photoconductor while leaving behind a latent electrostatic image in the non-illuminated areas. This latent electrostatic image may then be developed to form a visible image by depositing finely divided electroscopic marking particles called toner, which toner comprises coloring materials, such as dyestuffs or pigments, on the photoconductor.

Photoconductors for use in electrophotography are required to have the following fundamental characteristics:

(1) The photoconductors must be electrically chargeable to a predetermined potential in the dark.
(2) The photoconductors must retain the electrical charge sufficiently in the dark. In other words, the dark decay of the photoconductors must be small.
(3) The electrical charge on the photoconductors must be dissipated quickly under illumination. In other words, the light decay of the photoconductors must be great and, accordingly, the photosensitivity must be high.

In the production of organic photoconductors, it is required that organic photoconductor materials be dissolvable in solvents conventionally employed in this field, such as aromatic hydrocarbons including toluene and xylene; ketones including methyl ethyl ketone; heterocyclic compounds including dioxane and tetrahydrofuran; and halogenated hydrocarbons including methylene chloride and 1,2-dichloroethane; or mixtures of these solvents.

Furthermore, it is required that organic photoconductor materials be dissolvable in resins, such as polyethylene resin, polypropylene resin, polycarbonate resin, polyester resin and acrylic resin.

Still further, it is required that, when the photoconductor materials are employed as charge transport materials in photoconductors of a double-layered type, comprising a charge transporting layer and a charge generating layer formed on a support material, the charge transporting layer be transparent or nearly so. However, organic photoconductor materials which can meet the just described requirements are not many in number, particularly in the conventional carbazole derivatives.

For example, in Chemische Berichte (Berichte der Deutschen Chemischen Gesellschaft), Vol. 95 (1962), pages 2775 through 2781, there are disclosed 9-methylcarbazole derivatives. These derivatives, however, are not useful as photoconductor materials, since they cannot be dissolved in the above mentioned resins, and, in the case where those derivatives are dissolved in transparent resins, they tend to be crystallized, making the resin mixture opaque.

SUMMARY OF THE INVENTION

It is therefore an object of the present invention to provide carbazole compounds of the following formula (I)

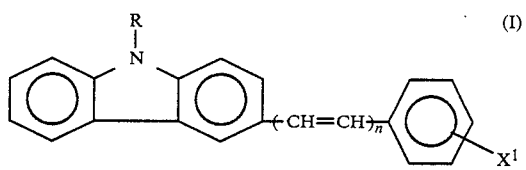

(I)

wherein R represents a $C_{2\sim4}$ alkyl group, or a benzyl group; $X^1$ represents hydrogen, a $C_{1\sim4}$ alkyl group, a $C_{1\sim4}$ alkoxy group, a halogen atom, a nitro group, an amino group, a $C_{1\sim4}$ alkylamino group or a benzylamino group; and n is an integer 1 or 2.

Another object of the present invention is to provide a process for preparing carbazole compounds of formula (II) by allowing phenyl derivatives of formula (III) to react with aldehydes of formula (IV)

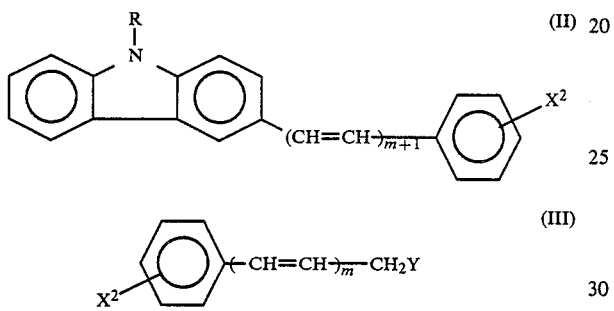

(II)

(III)

wherein $X^2$ represents hydrogen, a $C_{1\sim4}$ alkyl group, a $C_{1\sim4}$ alkoxy group, a halogen atom or a nitro group; m is an integer 0 or 1; and Y represents a triphenylphosphonium group of the formula

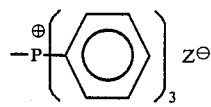

wherein $Z^\ominus$ represents a halogen ion, or Y represents a dialkylphosphonate group of the formula

—PO(OR')$_2$ wherein R' represents a $C_{1\sim4}$ alkyl group.

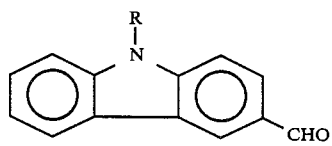

(IV)

wherein R represents a $C_{2\sim4}$ alkyl group, or a benzyl group.

The carbazole compounds according to the present invention meet the above-described requirements as photoconductor materials for use in electrophotography and are particularly useful as charge transport materials in photoconductors of a double-layered type, comprising a charge transporting layer and a charge generating layer formed on a support material, since they are dissolvable in the conventional solvents and conventional resins for forming the charge transporting layer, without making the layer opaque.

DETAILED DESCRIPTION OF THE PREFERRED EMBODIMENTS

A process for preparing the carbazole compounds of the formula (II) according to the present invention utilizes phenyl derivatives of the formula (III) as a starting material

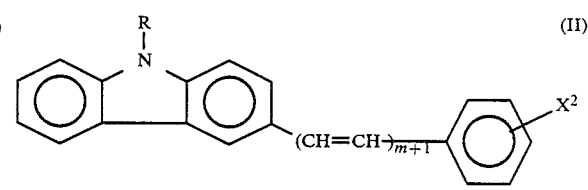

(II)

(III)

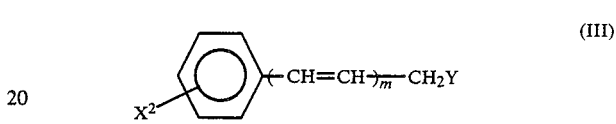

wherein $X^2$ represents hydrogen, a $C_{1\sim4}$ alkyl group, a $C_{1\sim4}$ alkoxy group, a halogen atom or a nitro group; m is an integer 0 or 1; and Y represents a triphenylphosphonium group of the formula

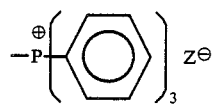

wherein $Z^\ominus$ represents a halogen ion, or Y represents a dialkylphosphonate group of the formula

—PO(OR')$_2$ wherein R' represents a $C_{1\sim4}$ alkyl group.

The above phenyl derivatives can be prepared easily by heating a mixture of a counterpart halomethyl compound of the phenyl derivatives, that is,

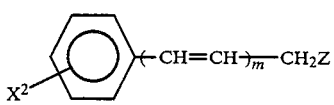

and a trialkylphosphite or triphenylphosphite, or by heating the mixture in a solvent, such as toluene or N,N-dimethylformamide (DMF).

As the trialkylphosphite, those containing an alkyl group having 1 to 4 carbons are preferable, and, in particular, a trialkylphosphite containing a methyl group or an ethyl group is most preferable.

The thus prepared phenyl derivatives of the formula (III) are allowed to react with aldehydes of the formula (IV), so that the above-described carbazole compounds of the formula (II) are prepared

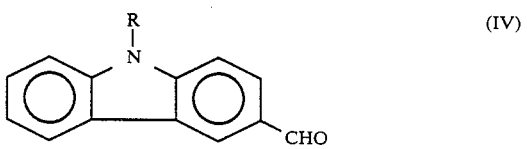

(IV)

wherein R represents a $C_{2-4}$ alkyl group, or a benzyl group, in the presence of a basic catalyst at temperatures ranging from room temperature to about 100° C.

As the basic catalyst, for example, sodium hydroxide, potassium hydroxide, sodium amide, and alcoholates, such as sodium methylate and potassium tert-butoxide, can be employed.

As the solvent for the above reaction, for example, methanol, ethanol, propanol, toluene, xylene, dioxane, N,N-dimethylformamide, dimethyl sulfoxide and tetrahydrofuran can be employed.

In the case where, of the compounds represented by the formula (III), a triphenylphosphonium derivative is employed in order to prepare the compound of the formula (II), after the completion of the condensation reaction, the reaction mixture is concentrated to the extent that the solvent for the reaction is decreased to 0% to 20% of its original volume. The reaction mixture is then washed with an aqueous solution of methanol containing 60% methanol, followed by the addition of a solvent, such as toluene, xylene, o-dichlorobenzene or DMF, and a small amount of iodine, and by the application of heat to the reaction mixture, whereby the yield of the compound of the formula (II) can be increased.

3-(4-aminostyryl)-9-ethyl-carbazole can be prepared by reduction of, for example, 3-(4-nitrostyryl)-9-ethyl-carbazole in a conventional procedure.

Furthermore, 3-(4-diethylaminostyryl)-9-ethyl-carbazole can be prepared by alkylation of, for example, 3-(4-aminostyryl)-9-ethyl-carbazole.

Examples of carbazole derivatives according to the present invention are as follows:

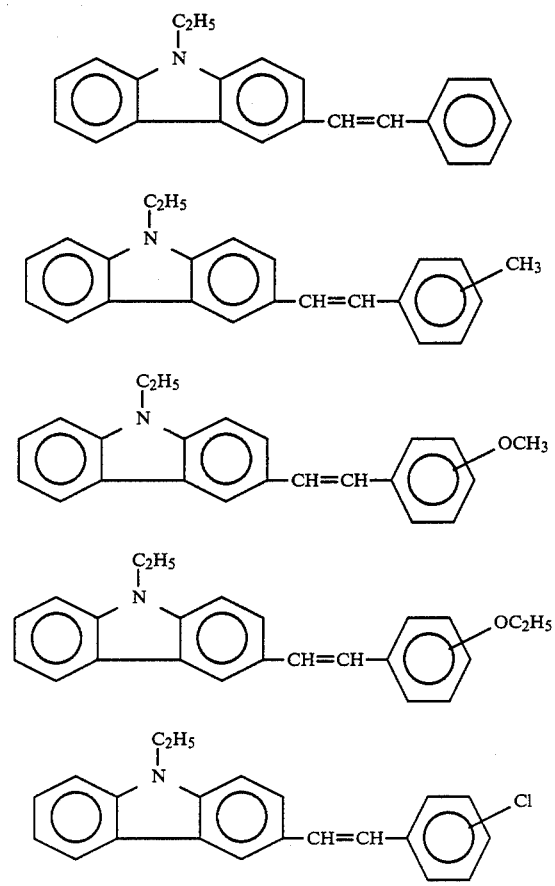

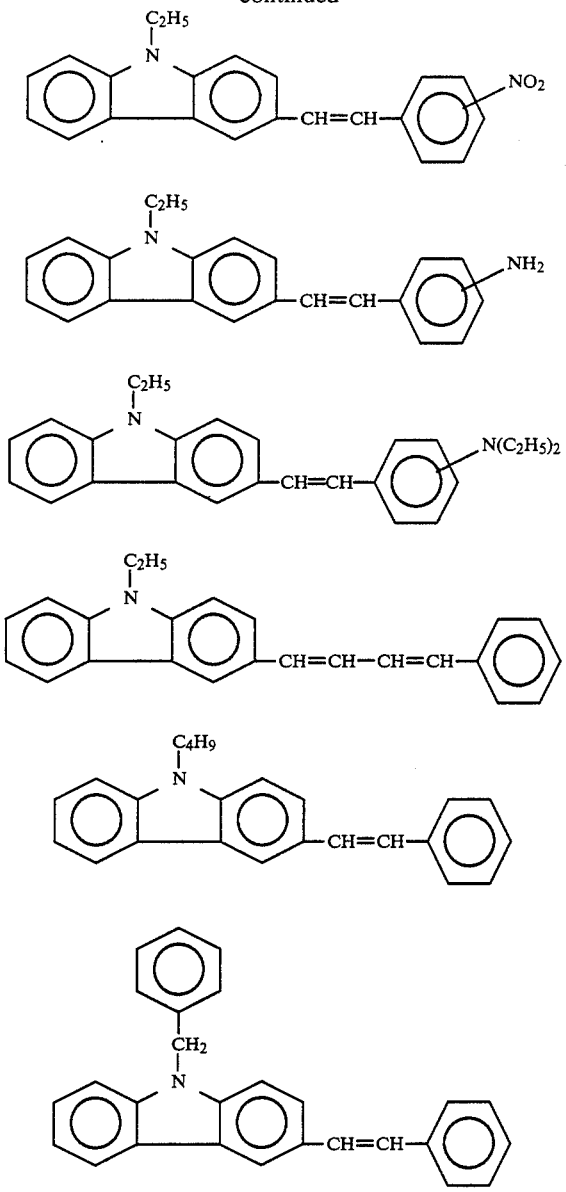

Embodiments of a carbazole derivative and a process for preparing the same according to the present invention will now be explained by referring to the following specific examples.

EXAMPLE 1

27.3 g (0.1 mole) of 4-nitrobenzyl-diethyl-phosphonate and 22.3 g (0.1 mole) of 3-formyl-9-ethyl-carbazole were dissolved in 200 ml of toluene. To this mixture was gradually added with stirring a solution consisting of 6.5 g (0.12 mole) of sodium methylate and 30 ml of methanol at room temperature. Upon the addition of the sodium methylate solution, orange crystals separated out. After further stirring the reaction mixture for 3 hours at room temperature, the crystals were filtered with suction and dried. The product thus obtained was recrystallized from toluene, so that 3-(4-nitrostyryl)-9-ethyl-carbazole with a melting point at 224.0° C. to 225.0° C. was obtained. The yield was 29.3 g (85.7% of the theoretical amount).

The reaction product was identified as the expected carbazole compound by elemental analysis, the results of which are shown in Table 1.

EXAMPLES 2 THROUGH 6

Example 1 was repeated except that, each time, the 4-nitrobenzyl-diethyl-phosphonate was replaced with one of a variety of phosphonates listed in Table 1, whereby a variety of novel carbazole derivatives were prepared as given in Table 1.

TABLE 1

| Example | Phosphoric Acid Derivative | Aldehyde | Product | Elemental Analysis Element | Calculated | Found | Melting Point (°C.) |
|---|---|---|---|---|---|---|---|
| 1 | CH₂PO(OC₂H₅)₂—C₆H₄—NO₂ | C₂H₅-N-carbazole-CHO | C₂H₅-N-carbazole-CH=CH—C₆H₄—NO₂ | C (%) H (%) N (%) | 77.17 5.30 8.18 | 77.04 5.43 8.11 | 224.0~225.0 |
| 2 | CH₂PO(OC₂H₅)₂—C₆H₄—CH₃ | C₂H₅-N-carbazole-CHO | C₂H₅-N-carbazole-CH=CH—C₆H₄—CH₃ | C (%) H (%) N (%) | 88.70 6.80 4.50 | 88.60 6.97 4.46 | 148.0~149.0 |
| 3 | CH₂PO(OC₂H₅)₂—C₆H₅ | C₂H₅-N-carbazole-CHO | C₂H₅-N-carbazole-CH=CH—C₆H₅ | C (%) H (%) N (%) | 88.85 6.44 4.71 | 89.02 6.51 4.70 | 117.5~118.5 |
| 4 | CH₂PO(OC₂H₅)₂—C₆H₄—OCH₃ | C₂H₅-N-carbazole-CHO | C₂H₅-N-carbazole-CH=CH—C₆H₄—OCH₃ | C (%) H (%) N (%) | 84.37 6.46 4.28 | 84.33 6.50 4.21 | 181.0~182.0 |
| 5 | CH₂PO(OC₂H₅)₂—C₆H₄—OC₂H₅ | C₂H₅-N-carbazole-CHO | C₂H₅-N-carbazole-CH=CH—C₆H₄—OC₂H₅ | C (%) H (%) N (%) | 84.42 6.79 4.10 | 84.38 6.91 4.04 | 145.5~146.5 |

TABLE 1-continued

| Example | Phosphoric Acid Derivative | Aldehyde | Product | Elemental Analysis | | | Melting Point (°C.) |
|---|---|---|---|---|---|---|---|
| | | | | Element | Calculated | Found | |
| 6 | CH$_2$PO(OC$_2$H$_5$)$_2$<br>—CH<br>=CH<br>—C$_6$H$_5$ | (4-CHO-phenyl)(2-(N-ethyl-N-phenyl)amino)phenyl | (4-(N-ethyl-N-phenylamino)phenyl)-CH=CH—CH=CH—C$_6$H$_5$ | C (%)<br>H (%)<br>N (%) | 89.13<br>6.54<br>4.33 | 89.04<br>6.58<br>4.29 | 117.5~118.5 |

EXAMPLE 7

34.2 g (0.1 mole) of 3-(4-nitrostyryl)-9-ethyl-carbazole, which was prepared in Example 1, and 28.0 g (0.5 mole) of iron powder were dispersed in 250 ml of DMF. To this dispersion was slowly added dropwise with stirring at room temperature a solution consisting of 14.2 ml (0.16 mole) of a 35% hydrochloric acid and 14.2 ml of water.

After stirring the mixture at 100° C. to 105° C. for 2 hours, an aqueous solution of sodium hydroxide consisting of 8.2 g (0.19 mole) of a 93% sodium hydroxide and 8.2 ml of water was added to the reaction mixture at room temperature. The reaction solution was filtered at 70° C. to 80° C. 1000 ml of water was added to the filtrate and crystals separated out, which were then filtered with suction and dried. The product thus obtained was recrystallized from toluene, so that 3-(4-aminostyryl)-9-ethyl-carbazole with a melting point of 167.5° C. to 168.5° C. was obtained. The yield was 22.0 g (70.5% of the theoretical amount).

The reaction product was identified as the expected carbazole compound by elemental analysis, the results of which are shown in Table 2.

EXAMPLE 8

31.2 g (0.1 mole) of 3-(4-aminostyryl)-9-ethyl-carbazole, which was prepared in Example 7, and 31.8 g (0.3 mole) of anhydrous sodium carbonate were dispersed in 230 ml of toluene. To this dispersion was slowly added dropwise with stirring at room temperature 46.2 g (0.3 mole) of diethyl sulfate. After stirring the mixture at 80° C. to 90° C. for 10 hours, an aqueous solution of sodium hydroxide consisting of 13.0 g (0.3 mole) of a 93% sodium hydroxide and 150 ml of water was added to the reaction mixture at room temperature. The reaction mixture was further stirred at 80° C. to 90° C. for 3 hours. An oil layer was separated from the reaction mixture. The solvent contained in the oil layer was removed. Crystals separated out in the oil layer, which were filtered with suction and dried. The product thus obtained was recrystallized from cyclohexane, so that 3-(4-diethylaminostyryl)-9-ethyl-carbazole with a melting point of 131.0° C. to 132.0° C. was obtained. The yield was 25.1 g (68.2% of the theoretical amount).

The reaction product was identified as the expected carbazole compound by elemental analysis, the results of which are shown in Table 2.

EXAMPLE 9

40.3 g (0.1 mole) of 2-methylbenzyl-triphenylphosphonium chloride and 22.3 g (0.1 mole) of 3-formyl-9-ethyl-carbazole were dispersed in 200 ml of toluene. To this dispersion was slowly added with stirring a solution consisting of 13.4 g (0.12 mole) of potassium tert-butoxide and 50 ml of methanol at room temperature. Stirring was continued at room temperature for 2 hours. After completion of the reaction, the solvent was removed from the reaction mixture, and the reaction mixture was washed with 200 ml of an aqueous solution of methanol containing 60% methanol. To the thus washed reaction mixture were added 200 ml of toluene and 6.3 g (0.05 mole) of iodine. The reaction mixture was stirred at 110° C. for 3 hours and was then cooled. Crystal separated from the reaction mixture were filtered with suction and dried. The product thus obtained was recrystallized from toluene, so that 3-(2-methylstyryl)-9-ethyl-carbazole with a melting point of 156.0° C. to 157.0° C. was obtained. The yield was 28.6 g (92.0% of the theoretical amount).

The reaction product was identified as the expected carbazole compound by elemental analysis, the results of which are shown in Table 2.

EXAMPLE 10

Example 9 was repeated except that the 2-methylbenzyl-triphenylphosphonium chloride was replaced with 2-chlorobenzyl-triphenylphosphonium chloride, whereby 3-(2-chlorostyryl-9-ethyl-carbazole was obtained.

The results of the elemental analysis and melting point are shown in Table 2.

EXAMPLE 11

Example 9 was repeated except that the 2-methylbenzyl-triphenylphosphonium chloride was replaced with 3-methylbenzyl-triphenylphosphonium chloride, whereby 3-(3-methylstyryl)-9-ethyl-carbazole was obtained.

The results of the elemental analysis and melting point are shown in Table 2.

TABLE 2

| Example | Product | Elemental Analysis | | | Melting Point (°C.) |
|---|---|---|---|---|---|
| | | Element | Calculated | Found | |
| 7 | 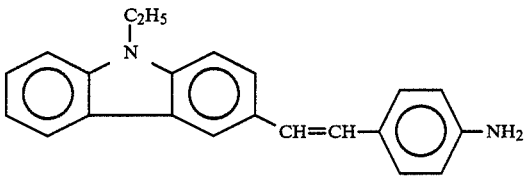 | C (%) <br> H (%) <br> N (%) | 84.58 <br> 6.45 <br> 8.97 | 84.50 <br> 6.56 <br> 8.93 | 167.5~168.5 |
| 8 | 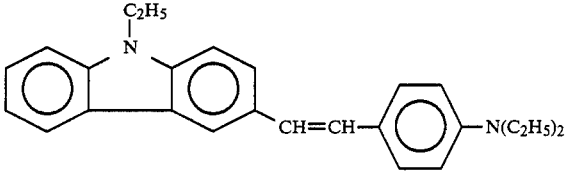 | C (%) <br> H (%) <br> N (%) | 84.74 <br> 7.66 <br> 7.60 | 84.59 <br> 7.72 <br> 7.51 | 131.0~132.0 |

TABLE 2-continued

| Example | Product | Elemental Analysis | | | Melting Point (°C.) |
|---|---|---|---|---|---|
| | | Element | Calculated | Found | |
| 9 | [carbazole with N-C₂H₅ and CH=CH-phenyl-CH₃ substituent] | C (%) <br> H (%) <br> N (%) | 88.70 <br> 6.80 <br> 4.50 | 88.60 <br> 6.99 <br> 4.48 | 156.0~157.5 |
| 10 | [carbazole with N-C₂H₅ and CH=CH-phenyl-Cl substituent] | C (%) <br> H (%) <br> N (%) <br> Cl (%) | 79.63 <br> 5.47 <br> 4.22 <br> 10.86 | 79.60 <br> 5.58 <br> 4.19 <br> 10.66 | 113.5~114.5 |
| 11 | [carbazole with N-C₂H₅ and CH=CH-phenyl-CH₃ substituent] | C (%) <br> H (%) <br> N (%) | 88.70 <br> 6.80 <br> 4.50 | 88.65 <br> 6.98 <br> 4.46 | 124.5~125.5 |

EXAMPLE 12

22.8 g (0.1 mole) of benzyl-diethyl-phosphonate and 25.1 g (0.1 mole) of 3-formyl-9-n-butyl-carbazole were dissolved in 100 ml of DMF. To this mixture was gradually added with stirring a solution consisting of 13.4 g (0.12 mole) of potassium tert-butoxide and 50 ml of DMF at room temperature. Stirring was continued at room temperature for 3 hours. The reaction mixture was then poured into 1000 ml of water. Crystals separated out. The crystals were filtered with suction and dried. The product thus obtained was recrystallized from toluene, so that 3-styryl-9-n-butyl-carbazole with a melting point of 84.0° C. to 85.0° C. was obtained. The yield was 27.4 g (84.3% of the theoretical amount).

The reaction product was identified as the expected carbazole compound by elemental analysis, the results of which are shown in Table 3.

EXAMPLE 13

Example 12 was repeated except that the 3-formyl-9-n-butyl-carbazole was replaced by 3-formyl-9-benzyl-carbazole, so that 3-styryl-9-benzyl-carbazole with a melting point of 172.0° C. to 173.0° C. was obtained. The yield was 28.8 g (80.2% of the theoretical amount).

The reaction product was identified as the expected carbazole compound by elemental analysis, the results of which are shown in Table 3.

TABLE 3

| Example | Product | Elemental Analysis | | | Melting Point (°C.) |
|---|---|---|---|---|---|
| | | Element | Calculated | Found | |
| 12 | [carbazole with N-C₄H₉ and CH=CH-phenyl substituent] | C (%) <br> H (%) <br> N (%) | 88.57 <br> 7.12 <br> 4.31 | 88.54 <br> 7.30 <br> 4.24 | 84.0~85.0 |

TABLE 3-continued

| Example | Product | Elemental Analysis | | | Melting Point (°C.) |
|---|---|---|---|---|---|
| | | Element | Calculated | Found | |
| 13 | | C (%) | 90.21 | 90.01 | 172.0~173.0 |
| | | H (%) | 5.89 | 5.95 | |
| | | N (%) | 3.90 | 3.88 | |

What is claimed:

1. A carbazole compound having the formula

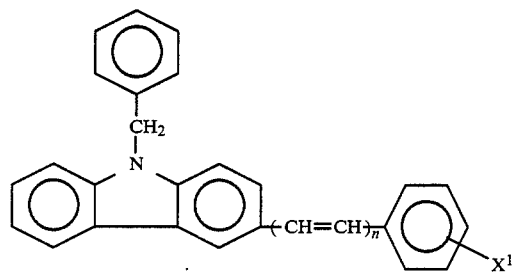

wherein $X^1$ represents hydrogen, a $C_{1-4}$ alkyl group, a $C_{1-4}$ alkoxy group, a halogen atom, a nitro group, an amino group, a $C_{1-4}$ alkylamino group or a benzylamino group; and n is an integer 1 or 2.

2. A carbazole compound having the formula

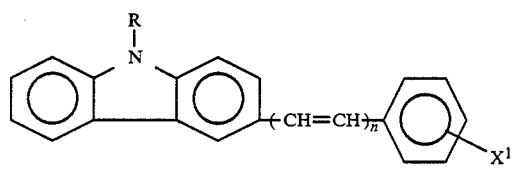

wherein R represents a $C_{2-4}$ alkyl group, $X^1$ represents a halogen atom, an amino group, a $C_{1-4}$ alkylamino group or a benzylamino group; and n is an integer 1 or 2.

3. A carbazole compound having the formula

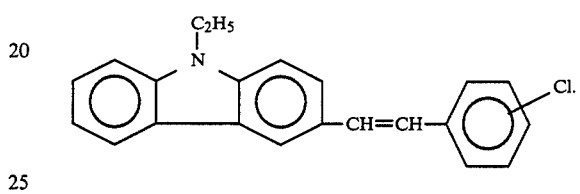

4. A carbazole compound having the formula

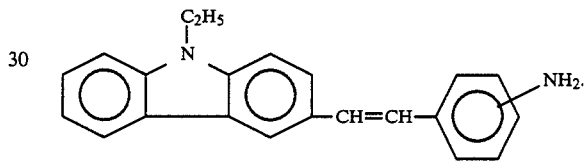

5. A carbazole compound having the formula

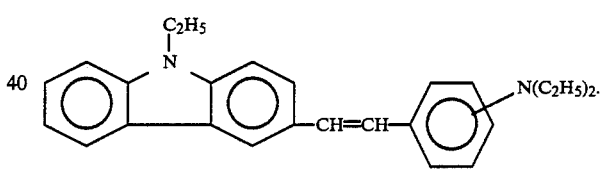

6. A carbazole compound having the formula

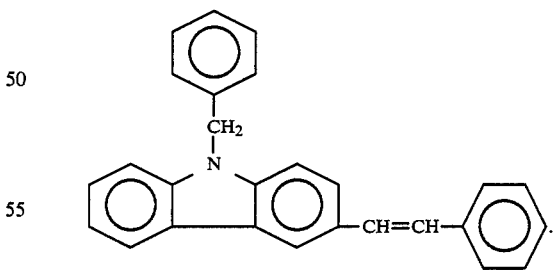

7. A carbazole compound according to claim 2 in which $X^1$ is benzylamino.

8. A carbazole compound according to claim 2 in which $X^1$ is $C_{1-4}$ alkylamino.

9. A carbazole compound according to claim 2 in which $X^1$ is amino.

10. A carbazole compound according to claim 2 in which $X^1$ is halogen.

* * * * *